US00PP21222P2

(12) United States Plant Patent
NeSmith et al.

(10) Patent No.: US PP21,222 P2
(45) Date of Patent: Aug. 24, 2010

(54) SOUTHERN HIGHBUSH BLUEBERRY PLANT NAMED 'TH-682'

(50) Latin Name: *Vaccinium sp.*
Varietal Denomination: TH-682

(75) Inventors: D. Scott NeSmith, Molena, GA (US); Mark Ehlenfeldt, Tabernacle, NJ (US)

(73) Assignees: University of Georgia Research Foundation, Athens, GA (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/380,261

(22) Filed: Feb. 25, 2009

(51) Int. Cl.
*A01H 5/00* (2006.01)

(52) U.S. Cl. ..... Plt./157

(58) Field of Classification Search ..... Plt./157
See application file for complete search history.

*Primary Examiner*—Susan B McCormick Ewoldt
(74) *Attorney, Agent, or Firm*—Davis Wright Tremaine LLP

(57) ABSTRACT

The new variety 'TH-682' is provided. The new and distinct variety ripens early compared to rabbiteye varieties generally available to homeowners and produces an abundance of attractive, light blue fruit that are generally large and have good flavor. The plant of the new variety 'TH-682' is vigorous, produces an attractive fall foliage color and is estimated to have a chilling requirement of approximately 500 to 550 hours below approximately 45° F. The asexually reproduced variety is reliably propagated vegetatively.

4 Drawing Sheets

STATEMENT REGARDING FEDERALLY-SPONSORED RESEARCH

This invention was made with U.S. Government support on behalf of U.S. Department of Agriculture, Hatch Act Grant No. GEO 01663. The U.S. Government has certain rights in this invention.

Latin name of the genus and species of the plant claimed: 'TH-682' is a southern highbush blueberry plant that is a *Vaccinium* sp. hybrid.

Variety denomination: The new southern highbush blueberry plant claimed is of the variety denominated 'TH-682'.

BACKGROUND OF THE INVENTION

The present invention relates to the discovery of a new and distinct cultivar of southern highbush blueberry plant botanically known as a *Vaccinium* sp. hybrid and herein referred to as 'TH-682', as herein described and illustrated.

The new blueberry plant variety 'TH-682' was selected in Griffin, Ga. in 2001. The new variety 'TH-682' ripens early compared to commercially available rabbiteye varieties and produces an attractive, light blue fruit. The fruit of the new variety 'TH-682' are generally large and have good flavor. The new variety 'TH-682' is vigorous with an estimated chilling requirement of between about 500 to about 550 hours below approximately 45° F. The new variety 'TH-682' also produces an attractive fall foliage leaf color.

Pedigree and history: The new blueberry plant variety 'TH-682' was selected in 2001 in Griffin, Ga. and originated from a cross of 'MS-122' (female parent, unpatented) by 'MS-6' (pollen parent, unpatented). The female parent 'MS-122' was produced by a cross between 'G-144' (unpatented) and 'US-121' (unpatented), and 'US-121' was produced by a cross between 'FL 4B' (an unpatented *Vaccinium darrowi* species) and 'Berkeley' (unpatented). The male or pollen parent 'MS-6' was produced by a cross between 'G-107' (unpatented) and 'Sharpblue' (unpatented). The new blueberry plant variety 'TH-682' has been tested since 2002.

The new variety 'TH-682' has been asexually propagated on many occasions since 2002 by softwood cuttings in Griffin, Ga. The new blueberry plant variety 'TH-682' has been shown to maintain its distinguishing characteristics through successive asexual propagations by, for example, softwood cuttings. Plants from softwood cuttings have been directly planted in the ground.

SUMMARY OF THE INVENTION

The new blueberry plant variety 'TH-682' has not been observed under all possible environmental conditions. The phenotype may vary somewhat with variations in environment and cultural practices such as temperature and light intensity without, however, any variance in genotype.

The following traits have been repeatedly observed in Alapaha and Griffin Ga., and are determined to be the unique characteristics of the new blueberry plant variety 'TH-682':

1. Excellent light blue fruit color;
2. Large berry size;
3. Excellent plant vigor;
4. Desirable fall foliage color.

The new variety 'TH-682' can be compared to 'O'Neal' (unpatented), another southern highbush as well as to early rabbiteye varieties such as 'Premier' (unpatented) and 'Climax' (unpatented).

Comparison to 'O'Neal' (unpatented). The new variety 'TH-682' is more vigorous than 'O'Neal', as demonstrated at locations in both Alapaha and Griffin, Ga., and typically produces larger berries that have better color reading. Flowers of the new variety 'TH-682' typically blooms about 10 to 14 days later than 'O'Neal', making the new variety 'TH-682' less susceptible to spring freezes during flowering. In addition, the berries of the new variety 'TH-682' are more firm than that of 'O'Neal', and ripen 7 to 10 days later.

Comparison to 'Premier' (unpatented). The new variety 'TH-682' typically produces berries with about the same size but with better color reading than 'Premier'. The new variety 'TH-682' typically flowers at the same time as 'Premier', however, the fruit of the new variety 'TH-682' ripen considerably earlier by about 14 to 18 days than 'Premier'. The period of ripening of the new variety 'TH-682', though too protracted to be suitable for typical commercial use, is desirable for homeowner use as the berries can be harvested over a longer period of time.

Comparison to 'Climax' (unpatented). The new variety 'TH-682' typically produces larger berries with better color reading than 'Climax'. Flowers of the new variety 'TH-682' typically bloom about 8 to 12 days later than 'Climax', and the fruit of the new variety 'TH-682' ripen considerably earlier by about 14 to 18 days than 'Climax'.

BRIEF DESCRIPTION OF THE FIGURES

The accompanying photographic illustration shows typical specimens in full color of the foliage and fruit of the new variety 'TH-682'. The colors are as nearly true as is reasonably possible in a color representation of this type.

BOTANICAL DESCRIPTION

Figure 1:
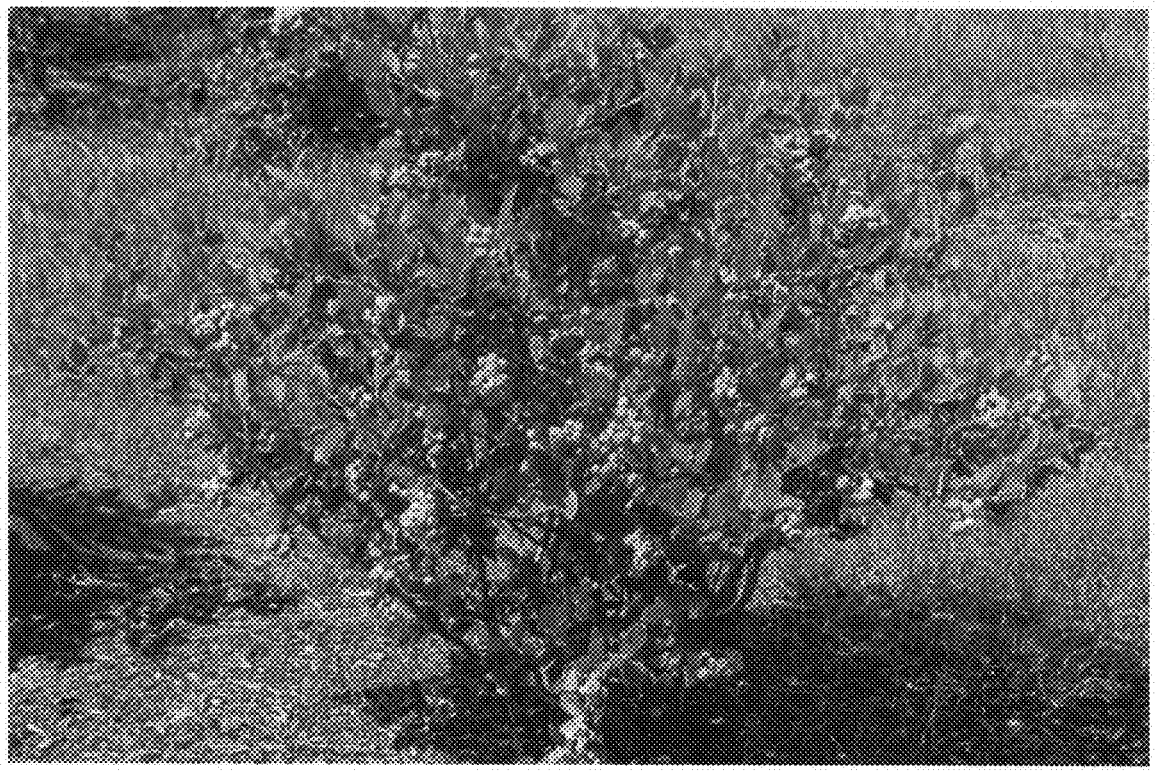
FIG. 1 is a photograph of the new variety 'TH-682'.
Figure 2:
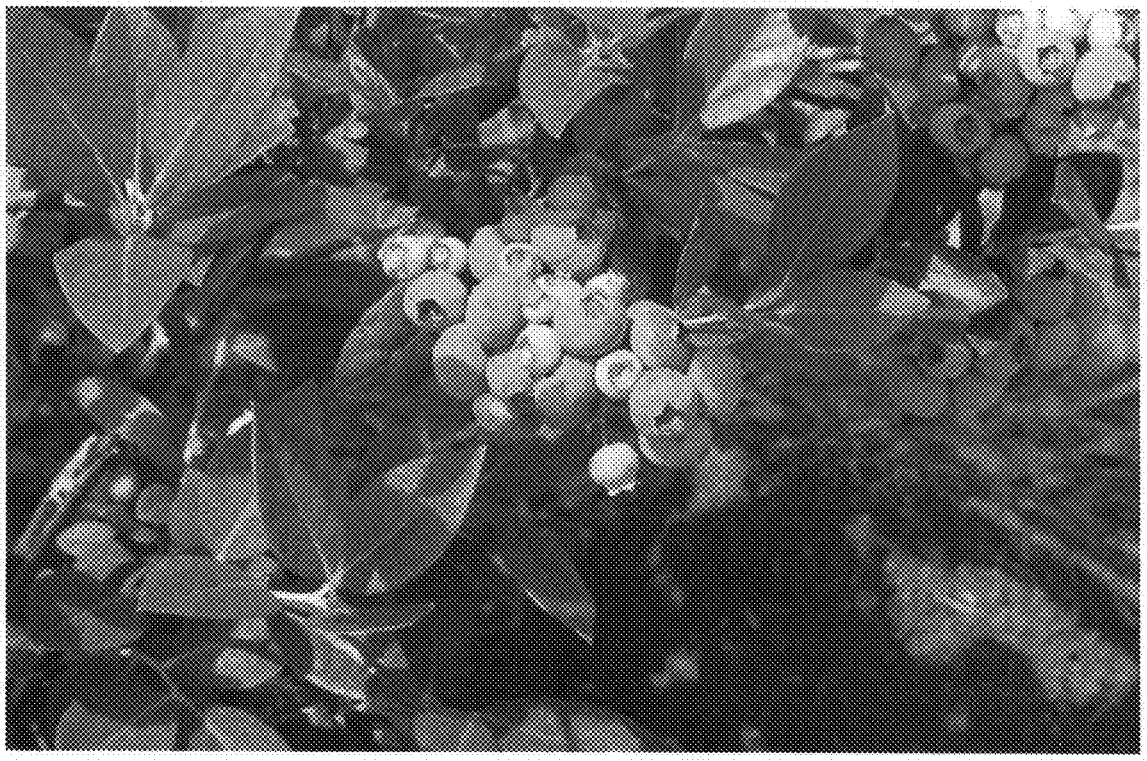
FIG. 2 is a photograph of the fruit of the new variety 'TH-682'.
Figure 3:
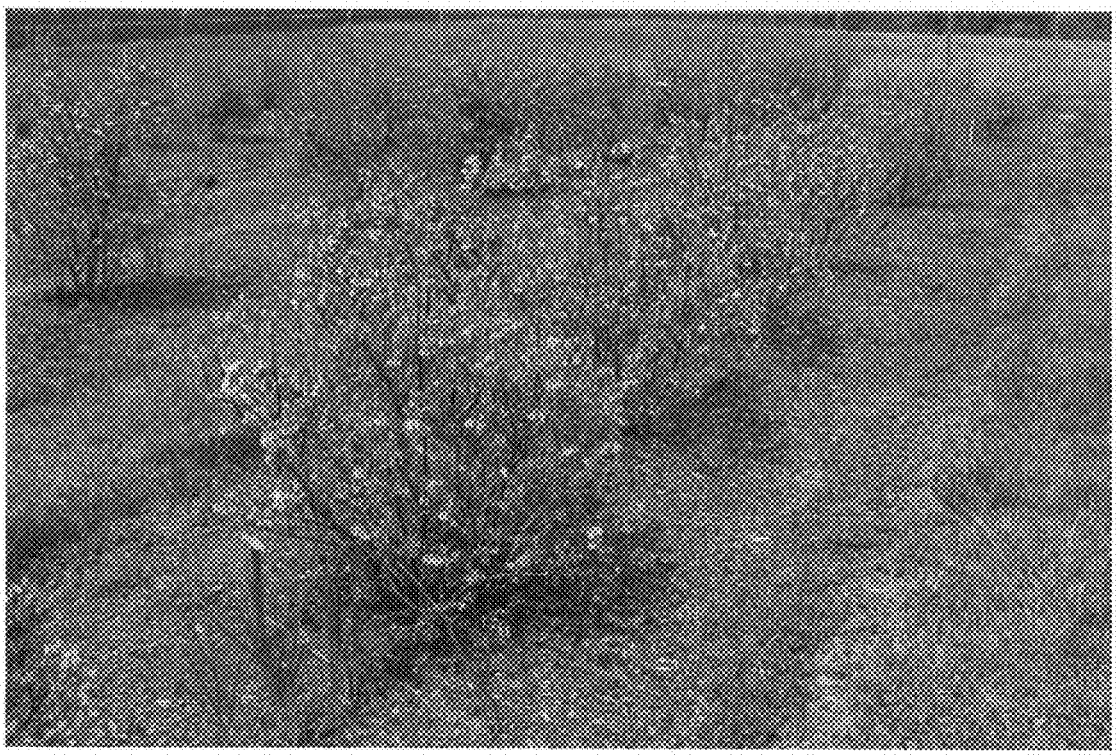
FIG. 3 is a photograph of the flowers of the new variety 'TH-682'.
Figure 4:
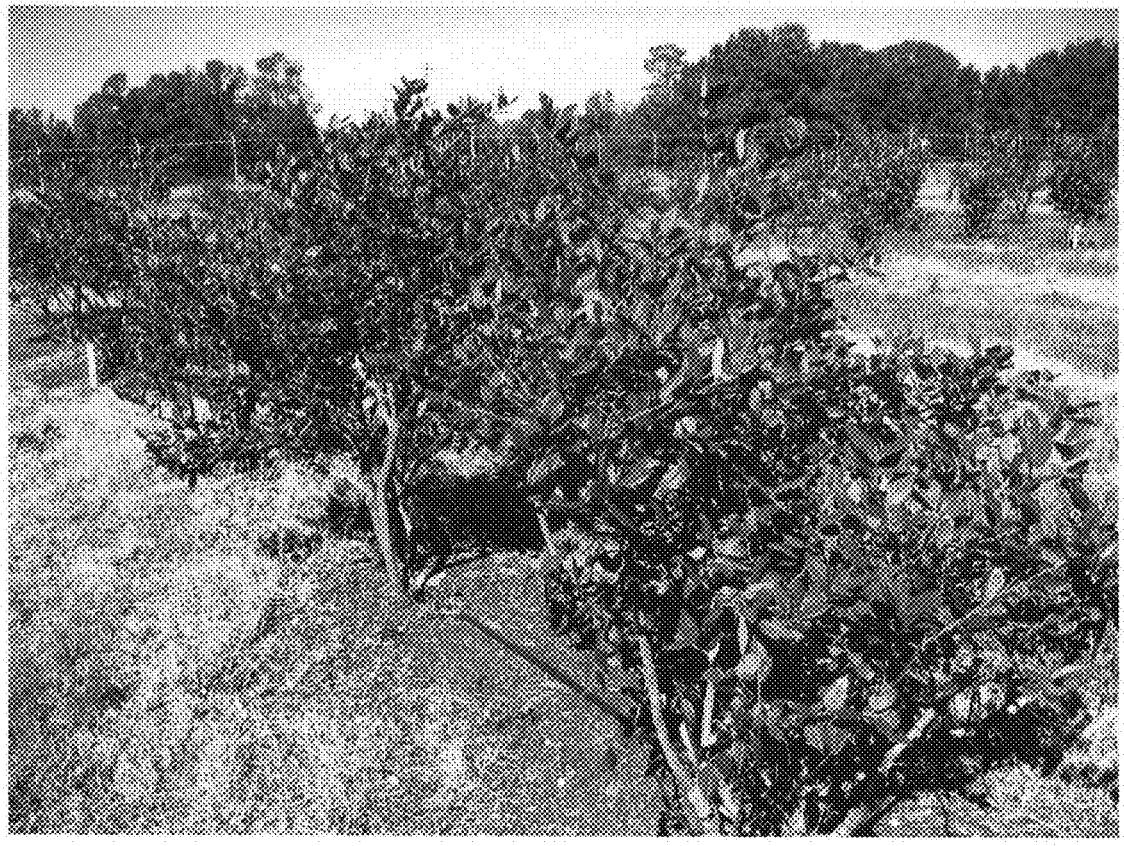
FIG. 4 is a photograph of the fall foliage color of the new variety 'TH-682'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and pomological characteristics of the new variety 'TH-682'. Where dimensions, sizes, colors, and other characteristics are given, it is to be understood that such characteristics are approximations and averages set forth as accurately as practicable. The descriptions reported herein are largely from specimen plants grown in Griffin, Ga., with supplemental irrigation. Plants were 5 years old.

The new variety 'TH-682' can self-pollinate, although increased fruit set and larger berry size typically result from cross pollination with another southern highbush variety. 'TH-682' has not been shown to be more or less susceptible to disease relative to other blueberry varieties. In other words, 'TH-682' has typical or average disease susceptibility/resistance for a southern highbush blueberry in Georgia.

PLANT

Size:

*Height.*—Approximately 1.2 to 1.4 m by about 4 years of age.

*Width at base or crown.*—Approximately 0.2 to 0.3 m.

*Width at top of bush.*—Approximately 1.0 to 1.2 m.

Growth habit: Strong upright growth habit. Narrow crowns, limited suckering.

Growth: High vigor; strong cane growth. Approximately five to seven main canes arising from base of plant.

Productivity: Medium to good, averaging approximately 5 lbs or more per plant for 4 year old plants grown with irrigation.

Hardiness: Similar to other southern highbush cultivars such as 'O'Neal' (unpatented). Expected range of adaptability USDA zones 6a to 9a.

Chilling requirement: Approximately 500 to 550 hours of temperatures at or below about 45° F. (about 7° C.) to induce normal leafing and flowering during the spring.

Leafing: Plants readily break numerous leaf buds simultaneously with anthesis in a chilling regime of approximately 700 hours or more.

Canes:

*Diameter.*—Approximately 20 to 30 mm in plants that are about 3 years old and older. Approximately 5 to 10 mm in about 2 year old wood.

*Color.*—About Greyed-Green RHS 197A to 197C in plants that are about 3 years old and older. About Yellow-Green RHS 145A in about 2 year old wood.

*Surface texture.*—Rough with some fissures and flaking bark in plants that are about 3 to 4 years of age, with texture becoming smooth as the plant ages. Smooth in plants that are less than about 3 years of age.

FOLIAGE

Leaf color: Healthy mature leaves.

*Top side.*—About Green RHS 137B.

*Under side.*—About Yellow-green RHS 148C.

Leaf arrangement: Alternate, distichous.

Leaf shape: Elliptic to ovate.

Leaf margins: Nearly entire, some with slight undulations.

Leaf venation: Reticulate.

Leaf apices: Broadly acuminate.

Leaf bases: Acute to nearly rounded.

Leaf dimensions:

*Length.*—Approximately 75 to 85 mm

Width.—Approximately 30 to 40 mm.

Petioles: Small.

*Length.*—Approximately 6.0 to 7.5 mm.

*Width.*—Approximately 2.0 to 3.0 mm.

*Color.*—About Yellow-Green RHS 145A.

FLOWERS

Date of 50% anthesis: March 28 (4 year average) in Griffin, Ga.

Flower shape: Urceolate.

Flower bud number: Medium to high. 'TH-682' typically produces 3 to 5 flower buds per fruiting twig. 1 flower bud per twig would be low, while 5 flower buds per twig would be high.

Flowers per cluster: Approximately 6 to 9.

Flower fragrance: Slight grass-like fragrance to none.

Corolla:

*Color.*—About Green-White RHS 157C (open flower).

*Length.*—Approximately 8.5 to 9.5 mm.

*Width.*—Approximately 8.5 to 9.5 mm.

*Aperture width.*—Approximately 4.0 to 5.0 mm.

Flower peduncle:

*Length.*—Approximately 14 to 18 mm.

*Color.*—About Yellow-Green RHS 145B.

Flower pedicle:

*Length.*—Approximately 5 to 7 mm.

*Color.*—About Green RHS 138B.

Calyx (with sepals):

*Diameter.*—Approximately 7.0 to 8.5 mm.

*Color.*—About Green RHS 138B.

Stamen:

*Length.*—Approximately 7.0 to 7.5 mm.

*Number per flower.*—Approximately 10.

*Filament color.*—About Yellow-Green RHS 144D.

Style:

*Length.*—Approximately 8.0 to 8.5 mm.

*Color.*—About Yellow-Green RHS 146D.

Pistil:

*Length.*—Approximately 10.0 to 11.0 mm.

*Ovary color (exterior).*—About Green RHS 138C.

Anther:

*Length.*—Approximately 4.3 to 4.5 mm.

*Number.*—Approximately 10.

*Color.*—About Greyed-Orange RHS 165B.

Pollen:

*Abundance.*—Medium.

*Color.*—About Yellow-Orange RHS 20B.

Self-compatibility: The cultivar has a moderate degree of self-compatibility.

FRUIT

Date of 50% maturity: June 3 (4 year average) in Griffin, Ga.

Fruit development period: Approximately 65 to 70 days.

Berry color:

*With wax.*—About Violet-Blue RHS 97C.

*With wax removed.*—About Black RHS 202A.

Berry surface wax abundance: Very high.

Berry flesh color: About Green-White RHS 157A.

Berry weight:

*First harvest.*—Approximately 1.9 g to 2.1 g.

*Second harvest.*—Approximately 1.6 g to 1.8 g.

Berry size:

*Height from calyx to scar.*—Approximately 13.0 to 15.0 mm.

*Diameter.*—Approximately 17.0 to 19.0 mm.

Fruit stem scar: Medium; medium dry; little or no tearing.

Berry firmness: Medium firmness.

Berry flavor and texture: Sweet mild flavor; excellent smooth eating texture.

Storage quality: Good.

Suitability for mechanical harvesting: Not suitable.

Uses: Primarily used as homeowner garden blueberry.

SEED

Seed abundance in fruit: Low to medium. 'TH-682' typically produces 10 to 20 well developed seeds per fruit. Less than 10 seeds per fruit is a low seed count, and greater than 20 seeds per fruit would be a high seed count.

Seed color: About Greyed-Orange RHS 165B.

Seed dry weight: Approximately 42.2 mg per 100.

Seed size: Approximately 1.5 to 1.8 mm long for fully developed seeds.

Three to five typical plants of the new variety 'TH-682', two rabbiteye varieties ('Climax' and 'Premier') and one southern highbush ('O'Neal') were compared over a three-year period (2004-2006) at Alapaha, Ga. and tested for certain properties. Rating scales are based on a 1 to 10 score, with 1 being the least desirable and 10 being the most desirable. Plant vigor is a relative scale (1 to 10) that considers overall robustness and durability of the plant itself (wood and vegetation). The approximate averages of these properties were as follows:

TABLE 1

COMPARISON OF 'TH-682' WITH OTHER BLUEBERRY PLANT VARIETIES AT ALAPAHA, GEORGIA

| Berry and plant attribute | 'TH-682' | 'Climax' | 'Premier' | 'O'Neal' |
|---|---|---|---|---|
| Berry size | 8.3 ± 0.4 | 6.7 ± 0.3 | 7.7 ± 0.4 | 6.8 ± 0.6 |
| Berry scar | 7.8 ± 0.6 | 8.3 ± 0.2 | 8.2 ± 0.2 | 7.0 ± 0.1 |
| Berry color | 9.5 ± 0.3 | 7.5 ± 0.3 | 8.0 ± 0.3 | 7.2 ± 0.2 |
| Berry firmness | 7.7 ± 0.2 | 8.3 ± 0.2 | 6.8 ± 0.1 | 6.7 ± 0.2 |
| Berry Flavor | 7.7 ± 0.2 | 7.8 ± 0.2 | 8.0 ± 0.1 | 7.7 ± 0.2 |
| Crop load | 4.8 ± 1.2 | 4.3 ± 1.6 | 6.0 ± 0.8 | 4.7 ± 1.3 |
| Plant vigor[Z] | 7.0 ± 0.1 | 8.5 ± 0.8 | 9.0 ± 0.1 | 6.0 ± 0.5 |
| Date of 50% flowering | March 21 | March 10 | March 18 | March 5 |
| Date of 50% ripening | May 24 | June 3 | June 6 | May 15 |

Three to five typical plants of the new variety 'TH-682', two rabbiteye varieties ('Climax' and 'Premier') and one southern highbush ('O'Neal') were compared over a three-year period (2004-2006) at Griffin, Ga. and tested for certain properties. Rating scales are based on a 1 to 10 score, with 1 being the least desirable and 10 being the most desirable. Plant vigor is a relative scale (1 to 10) that considers overall robustness and durability of the plant itself (wood and vegetation). The approximate averages of these properties were as follows:

TABLE 2

COMPARISON OF 'TH-682' WITH OTHER BLUEBERRY PLANT VARIETIES AT GRIFFIN, GEORGIA

| Berry and plant attribute | 'TH-682' | 'Climax' | 'Premier' | 'O'Neal' |
|---|---|---|---|---|
| Berry size | 8.1 ± 0.4 | 7.4 ± 0.3 | 8.1 ± 0.4 | 7.2 ± 0.7 |
| Berry scar | 7.0 ± 0.1 | 8.2 ± 0.1 | 7.5 ± 0.5 | 7.0 ± 0.1 |
| Berry color | 9.0 ± 0.3 | 7.9 ± 0.1 | 7.5 ± 0.5 | 6.9 ± 0.1 |
| Berry firmness | 7.3 ± 0.2 | 8.3 ± 0.1 | 6.9 ± 0.2 | 6.9 ± 0.1 |
| Berry Flavor | 7.7 ± 0.2 | 7.9 ± 0.1 | 8.0 ± 0.1 | 7.9 ± 0.1 |
| Crop load | 8.0 ± 0.3 | 7.3 ± 0.3 | 3.5 ± 1.5 | 5.5 ± 0.5 |
| Plant vigor[Z] | 8.3 ± 0.2 | 7.8 ± 0.1 | 8.0 ± 0.1 | 5.5 ± 0.5 |
| Date of 50% flowering | March 28 | March 25 | March 29 | March 18 |
| Date of 50% ripening | June 3 | June 15 | June 19 | May 26 |

What is claimed is:

1. A new and distinct variety of southern highbush blueberry plant named 'TH-682', substantially as illustrated and described herein.

* * * * *